(12) United States Patent
McMenimen et al.

(10) Patent No.: US 6,925,447 B2
(45) Date of Patent: Aug. 2, 2005

(54) RESPONSIVE MANUFACTURING AND INVENTORY CONTROL

(75) Inventors: James L. McMenimen, Ham Lake, MN (US); Christopher J. Campbell, Oakdale, MN (US); Barbara K. Ruble, Minneapolis, MN (US); Willa M. Fabian, Edina, MN (US); Larry G. Clark, Plymouth, MN (US); David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 294 days.

(21) Appl. No.: 09/775,281

(22) Filed: Feb. 1, 2001

(65) Prior Publication Data

US 2003/0061123 A1 Mar. 27, 2003

Related U.S. Application Data

(60) Provisional application No. 60/180,289, filed on Feb. 4, 2000.

(51) Int. Cl.$^7$ .............................................. G06F 17/60
(52) U.S. Cl. ........................................... 705/28; 705/22
(58) Field of Search ............................. 705/28, 22, 24; 607/30, 32; 128/903, 904

(56) References Cited

U.S. PATENT DOCUMENTS

| | | | |
|---|---|---|---|
| 5,113,869 A | 5/1992 | Nappholz et al. | ........... 128/696 |
| 5,336,245 A | 8/1994 | Adams et al. | ................. 607/32 |
| 5,345,362 A | 9/1994 | Winkler | ....................... 361/681 |

(Continued)

FOREIGN PATENT DOCUMENTS

WO   WO 01/56654 A1 * 8/2001

OTHER PUBLICATIONS

Majlesein et al. "Primary response of high–aspect–ratio thermoresistive sensors"Apr. 1997, Engineering Conference Title, v3068, p388–94 (file 2 #5837535).*

Dr. David M. Anderson, "Spontaneous Build–To–Order" Copyright 2001, http://www.design4manufacturability.com.*

James Carbone, "Most OEMs Build–To–Order" Apr. 1999, Purchasing Magazine Online.*

*Primary Examiner*—Lynda Jasmin
(74) *Attorney, Agent, or Firm*—Daniel G. Chapik; Girma Wolde-Michael

(57) ABSTRACT

A medical device production and supply information management system synchronous with manufacturing, planning and scheduling, product consumption forecast, and component purchase to enable just-in-time inventory control at the manufacturing facility, vendor stocks, material/product tracking, distribution and shipping management to thereby reduce inventory at all points in the product manufacturing, distribution/delivery chain. The system is implemented using a preferably Web enabled information network and data communications with a programmer. The programmer provides access to product information, specification and related data for implanted medical devices from which build-to-order and build-to-replenish commands are issued to the manufacturing center. The system is interactive within the consumption management system that is integrally and seamlessly connected with patients, hospitals, sales offices and related information hubs including manufacturing facilities. The invention enables management of inventory levels of medical devices through the interactive information management system by accurately accounting for inventory stored in sales offices, distributors and sales representatives, as well as implanting institutions to ensure that all centers have appropriate and adequate stock that is replaced on just-in-time basis under the build-to-replenish scheme.

1 Claim, 4 Drawing Sheets

U.S. PATENT DOCUMENTS

| | | | |
|---|---|---|---|
| D358,583 S | 5/1995 | Winkler | D14/106 |
| 5,611,051 A * | 3/1997 | Pirelli | 705/28 |
| 5,712,989 A * | 1/1998 | Johnson et al. | 705/28 |
| 5,725,559 A * | 3/1998 | Alt et al. | 607/5 |
| 5,752,976 A | 5/1998 | Duffin et al. | 607/32 |
| 5,891,180 A | 4/1999 | Greeninger et al. | 607/32 |
| 5,894,571 A | 4/1999 | O'Connor | 395/652 |
| 5,995,757 A | 11/1999 | Amberg et al. | 395/712 |
| 6,073,049 A * | 6/2000 | Alt et al. | 607/31 |
| 6,078,900 A | 6/2000 | Ettl et al. | 705/28 |
| 6,082,367 A | 7/2000 | Greeninger et al. | 128/899 |
| 6,298,443 B1 * | 10/2001 | Colligan et al. | 713/200 |
| 6,385,593 B2 * | 5/2002 | Linberg | 705/28 |
| 6,454,705 B1 * | 9/2002 | Cosentino et al. | 600/300 |
| 6,463,351 B1 * | 10/2002 | Clynch | 700/163 |
| 6,543,047 B1 * | 4/2003 | Vrhel et al. | 717/121 |
| 6,622,045 B2 * | 9/2003 | Snell et al. | 607/30 |
| 2002/0007294 A1 * | 1/2002 | Bradbury et al. | 705/7 |

* cited by examiner

RESPONSIVE MANUFACTURING AND INVENTORY CONTROL

This application claims priority to Provisional Patent Application No. 60/180,289 filed Feb. 4, 2000, and incorporates the specification and drawings in their entireties by reference herein.

FIELD OF THE INVENTION

The present invention relates to systems and methods of manufacturing medical devices. Specifically, the invention relates to an interactive system in which a manufacturing computer server interacts with various data centers or hubs to collect enabling information for various build-to-order scenarios. The system is interactive with an information management system that is integrally and seamlessly connected with patients, hospitals, sales offices, and related information hubs. More specifically, the manufacturing and inventory control system of the present invention provides an automated and interactive system which derives manufacturing requirements, on a real-time basis, for replacing medical devices and components which have recently been consumed or implanted based on inputs from the various information hubs connected to a web-enabled information communication system.

BACKGROUND OF THE INVENTION

Over the years, many implantable devices have been developed to monitor medical conditions and deliver therapy to a patient. Such devices included electrical stimulation devices for stimulating body organs and tissue to evoke a response for enhancing a body function or to control pain, and drug delivery devices for releasing a drug bolus at a selected site. Other more passive implantable and wearable medical devices have been developed for monitoring a patient's condition.

Chronically implanted cardiovascular devices for monitoring cardiovascular conditions and providing therapies for treating cardiac arrhythmias have vastly improved patients' quality of life as well as reduced mortality in patients susceptible to sudden death due to intractable, life threatening tachyarrhythmias.

Such implanted devices can also process the patient's electrogram and any measured physiological conditions employed in the diagnosis and store the data, for subsequent telemetry out on interrogation by the external programmer. In general, the manner of communicating between the transceivers of the external programmer and the implanted device during programming and interrogating is referred to as telemetry.

The short range of conventional device telemetry is itself viewed as unduly limiting the communication of information over a long distance. In the medical monitoring field, longer range, continuously accessible telemetry has been sought and systems for doing so have been proposed. In U.S. Pat. No. 5,113,869, Implantable Ambulatory Electrocardiogram Monitor to Nappholz, et al, for example, an implanted ambulatory ECG patient monitor is described that is provided with longer range telemetry communication with a variety of external accessory devices to telemeter out alarm signals and ECG data and to receive programming signals. The high frequency RF signals are encoded, including the implanted device serial number, to ensure that the communication is realized only with the proper implanted device and that it is not misprogrammed.

A remote, external programmer and analyzer as well as a remote telephonic communicator are also described that may be used in addition to, or alternately to, the personal communicator alarm and/or the full disclosure recorder. The programmer and analyzer may operate at a distance to the implanted AECG monitor to perform programming and interrogation functions. The implanted AECG may automatically transmit a beacon signal to the programmer and analyzer to initiate an interrogation function to transmit data to the programmer and analyzer on detection of an arrhythmia or a malfunction of the implanted AECG monitor detected in a self-diagnostic test. Or by setting a timer in the personal communicator alarm, the implanted AECG monitor may be automatically interrogated at preset times of day to telemeter out accumulated data to the telephonic communicator or the full disclosure recorder. The remote telephonic communicator may be part of the external programmer and analyzer and is automatically triggered by the alarm or data transmission from the implanted AECG monitor to establish a telephonic communication link and transmit the accumulated data or alarm and associated data to a previously designated clinic or physician's office through a modem.

A similar hand-held interrogator for an implanted pacemaker-cardioverter-defibrillator device is disclosed in U.S. Pat. No. 5,336,245, Storage Interrogation Apparatus for Cardiac Data, issued to Adams and Kroll in 1994, wherein the data accumulated in a limited capacity memory implanted device is telemetered out to a larger capacity, external data recorder. The accumulated data is also forwarded to a clinic employing an auto-dialer and FAX modem resident in a personal computer-based, programmer/interrogator.

U.S. Pat. No. 5,752,976, World wide patient location and data telemetry system for implantable medical devices, issued to Duffin, et al, in May 1998, referenced herein in its totality, is instructive for the present invention. This patent describes a system for communicating patient device information to and from a medical device implanted in an ambulatory patient and with a remote medical support network comprising: an implanted device telemetry transceiver within the implanted medical device for communicating data and operating instructions to and from the medical device in a coded communication, the implanted device telemetry transceiver having a transceiving range extending outside the patient's body a predetermined distance sufficient to receive and transmit coded telemetry communications at a distance from the patient's body; and an external patient communications control device adapted to be located in relation to the patient within the device transceiving range having a system controller for facilitating communications, an implant wireless interface including a control device telemetry transceiver for receiving and transmitting coded communications between the system controller and the implant device telemetry transceiver, a global positioning system coupled to said system controller for providing positioning data identifying the global position of the patient to the system controller; communications means for communicating with the remote medical support network; and communications network interface means coupled to the system controller and the communications means for selectively enabling the communications means for transmitting the positioning data to the medical support network and for selectively receiving commands from the medical support network. The medical support staff may initiate data/programming communications with the implanted medical device.

U.S. Pat. No. 5,891,180, Interrogation of an Implantable Medical Device Using Audible Sound Communication, to Greeninger et al, and U.S. Pat. No. 6,082,367, Audible Sound Communication from an Implantable Medical Device, to Greeninger and Thompson, both hereby incorporated by reference, are instructive on how data may be interrogated and telemetered out of the implanted device.

One of the issues unresolved by the '976 patent is the question of how to use this system to ensure that the implanting institution has an adequate inventory of implanted devices. If the information about inventory status at the implanting institution, such as the implantation of a medical device (a reduction in inventory) could be telemetered to the manufacturing site, the manufacturer could then build an identical device to replace the recently implanted device—a process called "build-to-order".

Build-to-Order manufacturing and control systems are well known to those familiar with the art. Such systems were pioneered by Dell USA, when the company's founder, as far back as 1985, began to manufacture and assemble computers to meet the needs of the user customer. This method of manufacturing and delivery of the product has been further enhanced by allowing potential customers to specify the exact type of desktop or laptop computer s/he wishes to purchase. Overhead, in the form of an outlet store with its accompanying sales personnel and incremental costs, are non-existent. As a result, Dell USA is able to consistently provide quality products at consistently lower costs, as compared to its competition. Dell USA holds well over 200 patents, many of which relate directly to the design and implementation of its build-to-order process. To mention but two such patents, we may cite U.S. Pat. No. 5,894,571 Process for Configuring Software in a Build-to-Order Computer System, issued to O'Connor, and U.S. Pat. No. 5,995,757 Software Installation and Testing for a Build-to-Order Computer System, both hereby referenced in their totality.

Another model that may be cited comes from IBM that holds U.S. Pat. No. 6,078,900 in June, 2000, Method for Estimating Stock Levels in Production-Distribution Networks with Inventory Control, issued to Amberg et al., also referenced herein in its totality. That invention provides computer software for business management and a computer implemented method for estimating stock levels in production-distribution networks with inventory control.

There are many similarities between the computer industry and the medical device industry. Thus, it should be possible to adapt and improve upon these well-known build-to-order systems and methods to fit the needs of the medical device industry.

Medical device industries are growing at a rapid rate with a corresponding rapid growth and change in their production processes. At present, the distribution of these products requires multiple stockholding points. One of the great challenges in the medical device environment is a company's ability to meet end-customer demand for an adequate inventory to provide immediate availability for medical devices for which the need cannot be predicted in advance. Consuming (implanting) devices prior to the expiration of a device's shelf life and managing the transition to newly approved devices (e.g., by the FDA) pose additional challenges.

If inventories are managed successfully, rewards can be tremendous. However, the penalty for keeping too little stock or failure to replace stock in a hospital goes beyond the cost of foregone revenue for both the manufacturer and the hospital. It includes the potential for loss of life because the individual required medical device is not available. The penalty for keeping too much stock in inventory, on the other hand, includes the cost of financing a large inventory thereby reducing profit margins to those medical institutions. Further, the need to implant products before obsolecense and managing a smooth transition into new products pose various strategic and manufacturing challenges. Furthermore, consuming (implanting) devices prior to the expiration of a device's shelf life and managing the transition to newly approved devices (e.g., by the FDA) pose additional challenges.

The initial stocking of inventory, as currently practiced, involves the manufacturer's representative and a person at the institution who is intimately familiar with the usage of medical devices and the number of devices used by the medical institution, often the hospital administrator. Assuming the institution has purchased a certain number of devices, the representative ensures that the institution has a certain number of these devices on the "shelves." The type of device and their number will reflect the nature and content of the contract governing the business relations, between the institution and the manufacturer and is usually based on expected, rather than actual, usage. Thus, there may be a distribution between basic, advanced, and more advanced technology, again conforming to the nature of the contract that governs the sale of such devices.

The manufacturer's representative maintains that initial inventory. If, however, and for one reason or another, the physician implanter has a greater number of patients who require the implantation of a medical device of one sort or another, the inventory of specific medical devices may become depleted. The situation often arises where the depletion of devices is not noticed until the physician requests a device to match the needs of the patient to be implanted the next day, or later in the day on which the request is made. What is to be done then? Usually a call is made to the manufacturer's local business office that may or may not have the exact model on hand. If so, someone has to bring it to the institution. This may involve many miles depending on the location of the business office relative to the medical institution. If this device is not available at the local business office, a call will be made to the manufacturer's central office or to the manufacturing facility. In such cases and even when Herculean efforts take place, the device will not usually arrive at the institution in time for the original scheduled implant. Often the implant must be postponed for several days. This is the primary issue that the present invention addresses.

A secondary issue that must be addressed occurs during those times when the device manufacturer is introducing a new product. The manufacturing facility must have on hand a rather large number of newer devices which the physicians and institutions will request for use upon approval for implant is received from an approving agency such as the FDA in the U.S.A. and other such agencies in Europe and Japan. Yet, until approval is given, none of the newer devices may be implanted. Only those that were previously approved may be implanted. If the approval is delayed for one reason or another, the manufacturer must maintain two inventories, one of the older and one of the newer product lines. In such cases, when approval is finally granted and because the physicians usually wish to make use of the newer technology, the manufacturer must usually retrieve the older product inventory and dispose of it in some way or other, usually at an economic loss to the manufacturer which, in turn, can bring about a subsequent increase in cost to the government, insurance payer, or patient.

The key challenge that the medical device industry must face is to determine where and in what quantities to hold safety stock in the network so as to protect against uncertainties, and to ensure that target customer service levels are met. Aggressive service requires significant inventory planning. Today, the determination of inventory levels is localized and often ad hoc, and not based on an analysis of optimal levels and deployment. As a result, the business impact, in terms of the trade-off between inventory investment and customer serviceability or delinquency, is far from optimal.

Determining the optimal inventory levels in individual medical institutions is extremely difficult, and few real-world inventory management systems have the capability to accurately predict target stock levels. The difficulty of the problem arises from the fact that the quantity of safety stock held at one stocking location, and the policy determining replenishment of inventory at that location, will affect other stockholding locations in the network. A system is needed that accurately represents the interdependencies of all links in a production-distribution network, and allows the manufacturer of medical devices to fill the institution's inventory on an automatic basis whenever that inventory is depleted by even one device as it is used.

Modern medical devices contain highly sophisticated hardware and software components that require specialized manufacturing processes. Further, these same devices require replacement on the shelves of a hospital on a timely basis when a unit in inventory is implanted in a patient. Hospitals, physicians, and other patient-care systems operate in a highly constrained economic environment. Inventory control is one way to reduce costs within these medical systems. Thus, a medical device manufacturing system that is interactive with and responsive to this environment is highly desirable. This is especially true if such a system can minimize the need for maintaining a large inventory of these medical devices, while sustaining the institution's ability to deliver efficient and effective medical care.

What is needed is a system that has the following goals: build products to refill the medical institution's inventory order, automatic replenishment of stock in days, and track manufacturing and product information in order to effectively service customers.

SUMMARY OF THE INVENTION

This invention builds on the previously filed application Ser. No. 09/430,208, Automatic Invoice Upon Pacemaker Implant by Linberg on Oct. 29, 1999, hereby referenced in its totality, which describes an auto-invoicing system. With the data acquired with this system, the present invention makes it possible to manage inventory levels of products implanted ("consumed"). On the one hand, this invention manages inventory at any place products are stored, such as in sales offices, with individual sales representatives, and ultimately at the implanting institution to ensure that the appropriate and adequate stock is quickly replaced on just-in-time basis always available. These devices include—but are not limited to—implantable pacemakers, cardioverter-defibrillators, neurological stimulators, leads, drug delivery systems, lead adapters, lead repair kits, etc. On the other hand, this invention may be used to control and manage manufacturing planning and scheduling, forecasting product consumption, purchasing device components, inventory control at the manufacturing facility, vendor management, material tracking, capacity planning, distribution and shipping of finished product, etc.

The required data, for example that a specific device with its associated lead(s), has been implanted may be transferred by the programmer to the Information Network, described in the '976 patent. These data may be downloaded on a real time basis or on a daily basis, usually at night. The Information Network will then summarize these data on a daily basis and issue a built order to replenish the stock that was "consumed" at implant for the specific implanting institution. Specifically, the device type, model number, serial number, name of the implanting physician, the name of the sales representative, the name of the implanting institution are automatically downloaded to the Information Network through the programmer, as substantially described in U.S. Pat. No. 5,345,362 and Des. 358,583 by Winkler, both of which are incorporated by reference in their entirety. These data, when received, would in turn automatically initiate a "build-to-order" replenishment to match and replace the device(s) implanted at that institution.

Although the intention of this process is to have a very quick turnaround time, e.g., a total of two days from notification of implant, building the product in an automated assembly line, and delivery of the product, it is also possible that the status of the product build could be made available to all interested parties (purchase agent, physician, hospital administrator, sales rep, etc.) on an ongoing basis. Other benefits would include substantial cost savings in manufacturing, reduced product cycle times, reduced obsolescence, reduced inventories at all points in the product delivery chain, and so on. This process will minimize inventory issues for the account, as well as for the manufacturer. In addition it will make it easier to ramp up for the introduction of a new product while, at the same time ramping down the build of the old product. "Phase out" should be much simpler and quicker. With the attainment of these benefits, the costs to the implanting institution can also be controlled and reduced significantly.

Using this invention, the implanting institution's inventory is automatically managed. For example, the Information Network could recommend an alternative device to replace a "used" device. This might occur when products are being phased in or phased out or when a new product is approved for implantation by the specific approving agency in a geographic area. Automatic notifications, based on local regulatory controls, could be placed on labels or within the shipping package so that restrictions on the product's usage, warnings, alerts, etc. could be communicated and implemented. Additionally, the institution and/or implanting physician will be able to monitor the status of the build process, the expected completion, and the status of shipping and scheduled delivery, all of which is commonly known and expected in the shipping industry (i.e., Federal Express or UPS tracking systems).

DETAILED DESCRIPTION OF THE DRAWINGS

The present invention uses the Global Communications and Monitoring System (GCMS) described in the '976 patent. This system provides a means for exchanging information with and exercising control over one or more medical devices implanted within the body of a patient employing the patient communications control device. The GCMS is intended to function no matter how geographically remote the patient may be relative to the monitoring site or medical support network. As such, then, during the implant procedure, with the patient in very close proximity to the programmer, there should be no difficulty in establishing communications between the implanted device and the programmer. In this situation, the programmer determines location and details relevant to the device communicates those data via a cellular telephone system link or a satellite based telecommunications link if the patient is outside the range of a cellular link or subscribes only to the satellite-based link.

Figure 1:
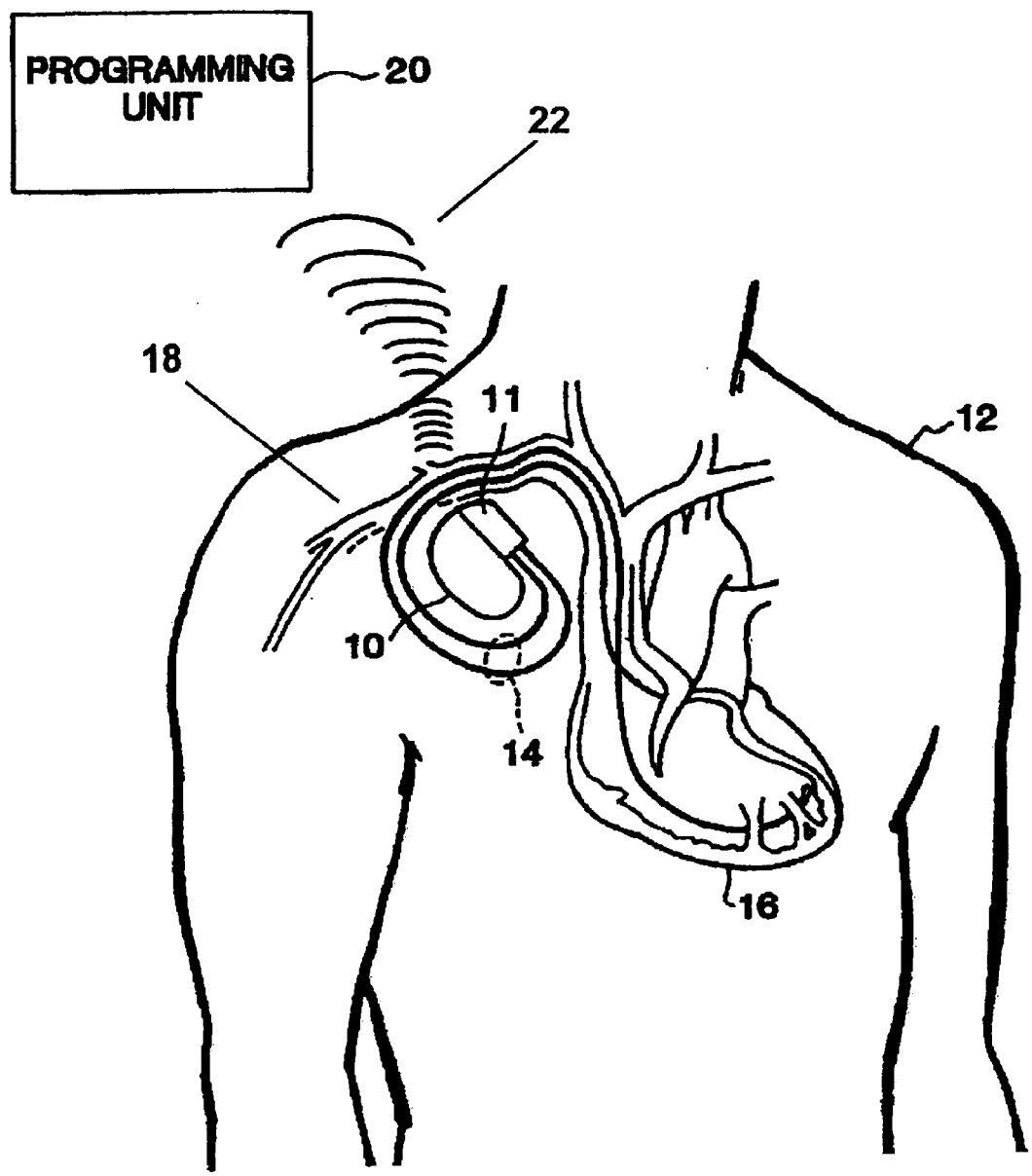
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker for illustration purposes—that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16.

Although the present invention will be described herein in an embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art. In addition, programmer 20 is also equipped with a transceiver and/or modem to facilitate communication between programmer 20 and the Internet.

Figure 2:
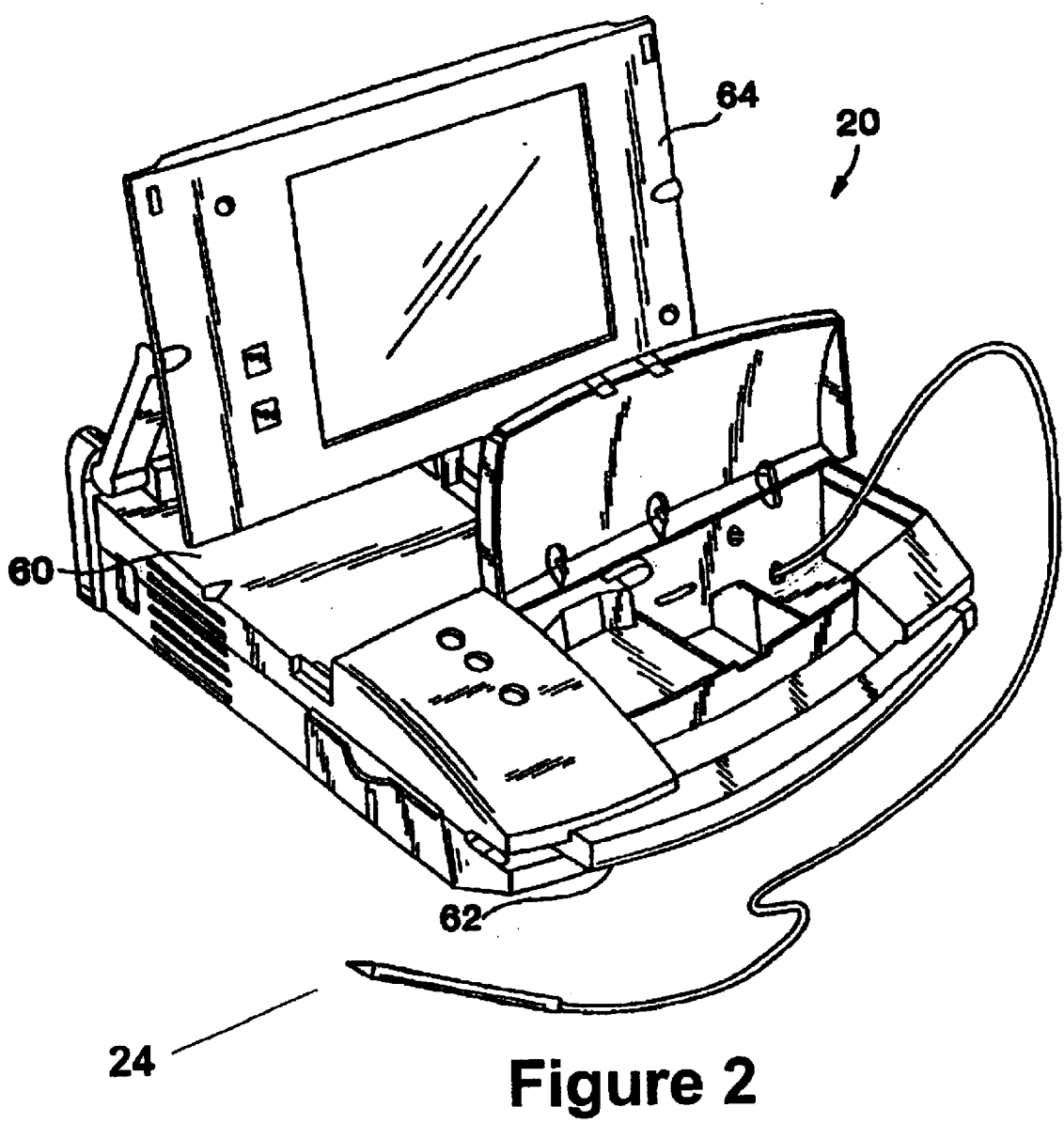
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art. In addition, there is a transceiver (not shown) that is used to communicate data wirelessly (telemetry) from the implanted device to an Information Network (see FIGS. 3 and 4). Alternatively, a modem and landlines may be used.

The FCC has adopted the following definition for describing wireless medical telemetry: "the measurement and recording of physiological parameters and other patient-related information via radiated bi- or unidirectional electromagnetic signals." Thus, in its broadest sense, telemetry can be defined as the art and science of conveying information from one location to another. With radio telemetry, radio signals are utilized to convey that information.

"Telemedicine" is the use of telecommunications and information technology to provide clinical care or data at a distance. The definition of "distance" may range from several yards, such as might occur within a clinic environment or hundreds of miles as occurs in transmission of such data between an implanting institution and an Information Network, as envisaged in the present invention. Wireless technology can be particularly beneficial because developing wireless networks may be faster and cheaper than building a landline infrastructure.

Medical telemetry equipment is increasingly relied upon in hospitals to improve health care and reduce costs. The number of pacemaker patients with chronic medical conditions is rising due to the growth in the elderly population. For these reasons, the need for ensuring the availability of an adequate inventory of pacemakers within the implanting hospital is vital and this need can be fulfilled with medical telemetry equipment such as that used in the programmer depicted in FIG. 2

Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof. Stylus 24 is used for data entry and/or control of programmer 20.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads. These leads may be rendered redundant if the implanted device is equipped with a "subcutaneous electrode array" as described in the filed application Ser. No. 09/749,169, Leadless Fully Automatic Pacemaker Follow-Up, by Combs et al., filed Dec. 12, 2000.

Programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in the previously cited U.S. Pat. No. 5,345,362. The Medtronic Model 9790 programmer is the implantable device-programming unit with which the present invention may be advantageously practiced.

Figure 3:
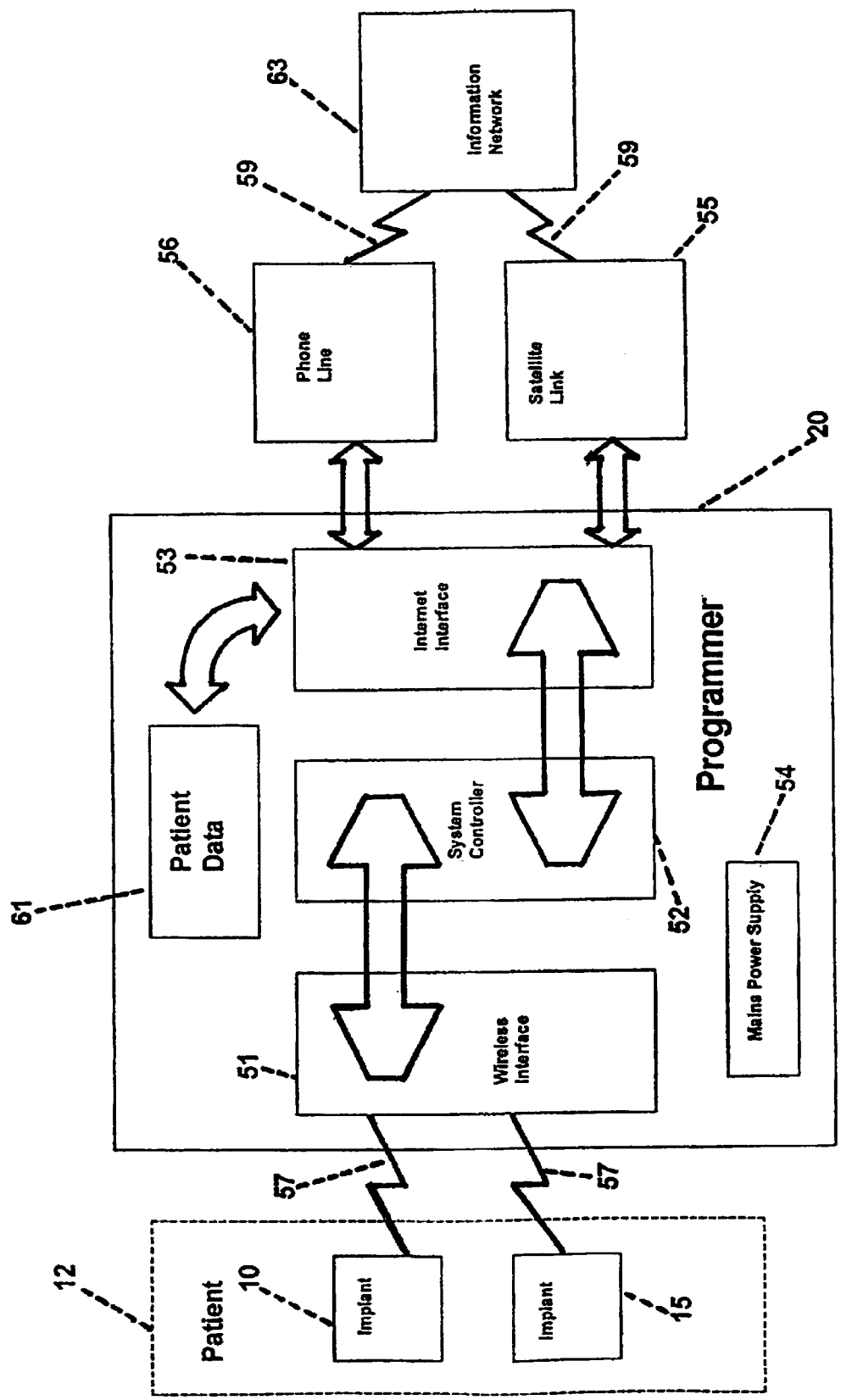
FIG. 3 is a block diagram of a system in which the invention is practiced for a patient receiving an implantable medical device, in communication with a programmer, which is in communication with the Information Network employing Internet telecommunication and/or satellite linkage.

FIG. 3 is a block diagram of a system in which the invention is practiced. The major components of the system include at least one implanted medical device patient 12, programmer 20, and Information Network 60. Patient 12 may have multiple implants, for example, an implanted bradycardia type pacemaker 10 with and an implanted ICD 15 that has just been implanted. ICD 15, preferably communicates through RF link 57 to the programmer, specifically to wireless interface 51. Data, such as factory-programmed parameters and so on, are forwarded to system controller 52. Under a physician's direction/prescription, these parameters may be altered and downloaded from system controller 52 to ICD 15 via RF wireless interface 51.

Continuing with FIG. 3 and more to the point of its relation to the present invention, we see that the same data as well as the device's model number, serial number, date of implant, and so on are conveyed to system interface 53. At this juncture, the data may be stored (in patient data memory 61) or transmitted/telemetered immediately. The time of transmission is dependent on whether the programmer is or is not connected to phone link 56 or satellite link 55 at the time of implant. Assuming that one of these connections is made at some time during the day, the data from patient data 61 and Internet interface 53 is uplinked to the Internet via phone line modem connection 56 and phone line 59 or telemetric satellite link 55 using data encryption technology for a secure transmission as substantially described in filed application Ser. No. 09/431,881, Method and Apparatus to Secure Data Transfer from Medical Device Systems, filed Nov. 2, 1999 by Nichols and incorporated herein by reference. Upon reaching Information Network 63, these data are incorporated into the data file containing the complete information relating to the implanting institution, for billing purposes and other uses. These same data are also forwarded to that portion of the network computer related to new build orders for manufacturing, which relates to FIG. 4.

Figure 4:
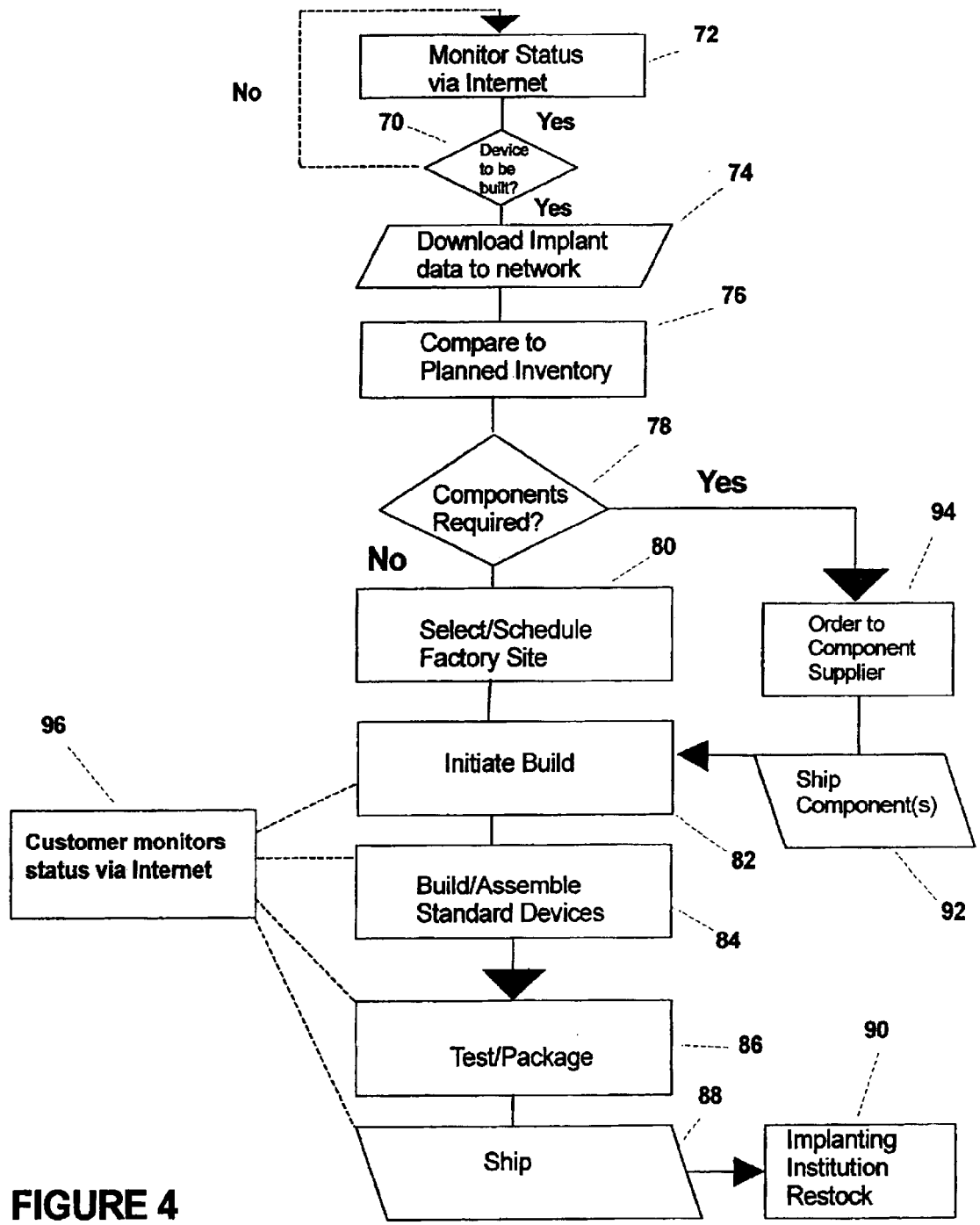
FIG. 4 is a block diagram of the present invention describing the multiple steps that occur in the manufacturing facility from receipt of the order to shipment of the device to the implanting institution.

Turning our attention now to FIG. 4, we see the various steps used during the manufacturing process to ensure that the recently implanted ICD (using the example mentioned above) is replaced as quickly as possible. Once an implant has taken place at a particular institution the data is available to the Information Network 63 (see FIG. 3), that same network, which is constantly monitoring the "build-to-order" status 72. The network periodically determines whether a device needs to be built 70 for this particular institution. If No, then it continues to monitor for an implant. If Yes, then the implant data is downloaded to the manufacturing database 74. This includes all pertinent data relative to the implanted device. Specifically, these data will include the device type, model number, serial number, name of the implanting physician, the name of the sales representative, and the name of the implanting institution. These data, when received, will automatically initiate a "build-to-order" replenishment to match and replace the standard device(s) implanted at that institution.

Once the order is made, a comparison is made to assess whether the build will meet the planned inventory 76. In addition, the manufacturing database will determine whether all components required to complete the build are available 78 at the factory site located nearest to the implanting institution. If components are available, that factory site is selected and scheduled to complete the build 80. If components are not available, the manufacturing database issues an automatic component supplier order 94. The required components are noted and shipped by the supplier(s) 92 to the manufacturing site.

Initiating build 82 with available components or those delivered from the supplier results in building and assembly of the "standard" device, which will replace the implanted device in the inventory of the implanting institution. The implantable device is tested at various stages in the manufacturing process 84 and will undergo final testing prior to packaging 86 and sterilization. Finally, the device is shipped 88 to the implanting institution 90 for restocking in their inventory.

During this whole process, the purchasing agent and/or hospital administrator is able to discern exactly the stage that the device being manufactured has reached. Such information will be available on the Information Network that is accessed via the Internet 96. This same access to the Information Network is also available to the sales representative who is able to monitor the progress of the build and report to the implanting institution, if that institution is unable to access the Information Network—for whatever reason.

As previously mentioned, the goal for this Responsive Manufacturing and Inventory Control system is to deliver a replacement device within two working days of receipt of the information that a device has been implanted and must be replaced.

The preceding specific embodiments are therefore to be understood as illustrative of the many ways in which the principles of the invention may be practiced. It is to be understood, therefore, that other expedients known to those of skill in the art or disclosed herein may be employed without departing from the invention or the scope of the appended claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

It is therefore to be understood, that within the scope of the appended claims, the invention may be practiced otherwise than as specifically described without actually departing from the spirit and scope of the present invention.

What is claimed is:

1. A medical device inventory and production control system comprising:

a Web-enabled information network in data communications with a medical device manufacturing control system and a consumption hub;

at least one programmer in a bi-directional telemetric data communication with the Web-enabled information network; and at least one implantable medical device taken out of an inventory of the consumption hub, the medical device having a data set communicated via the medical device programmer through the Web-enabled information network to the medical device manufacturing control system which initiates a build to order process based upon the data communicated from the medical device programmer to replace the inventory of the consumption hub depleted by the at least one implantable medical device taken out of the inventory of the consumption hub.

* * * * *